(12) United States Patent
Yamaguchi et al.

(10) Patent No.: US 11,452,842 B2
(45) Date of Patent: Sep. 27, 2022

(54) MEDICAL INSTRUMENT, CATHETER, AND METHOD FOR PRODUCING MEDICAL INSTRUMENT

(71) Applicant: SUMITOMO BAKELITE CO., LTD., Shinagawa-ku (JP)

(72) Inventors: Kenjiro Yamaguchi, Akita (JP); Kenichi Kanemasa, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 700 days.

(21) Appl. No.: 14/772,237

(22) PCT Filed: Mar. 7, 2014

(86) PCT No.: PCT/JP2014/055958
§ 371 (c)(1),
(2) Date: Sep. 2, 2015

(87) PCT Pub. No.: WO2014/136937
PCT Pub. Date: Sep. 12, 2014

(65) Prior Publication Data
US 2016/0001040 A1 Jan. 7, 2016

(30) Foreign Application Priority Data
Mar. 8, 2013 (JP) .............................. JP2013-046335

(51) Int. Cl.
*A61M 25/00* (2006.01)
*A61M 25/01* (2006.01)

(52) U.S. Cl.
CPC ...... *A61M 25/0053* (2013.01); *A61M 25/005* (2013.01); *A61M 25/0012* (2013.01);
(Continued)

(58) Field of Classification Search
CPC ............ A61M 25/005; A61M 25/0147; A61M 25/0045; A61M 25/0662; A61M 25/0012; A61M 25/00
See application file for complete search history.

(56) References Cited

U.S. PATENT DOCUMENTS 5,571,085 A    11/1996  Accisano, III
6,126,650 A *  10/2000  Martinez ........... A61M 25/0054
                                                      604/264
(Continued)

FOREIGN PATENT DOCUMENTS

JP    2006 192269    7/2006
JP    2011 505974    3/2011
(Continued)

OTHER PUBLICATIONS

International Search Report dated Apr. 15, 2014 in PCT/JP14/055958 Filed Mar. 7, 2014.

*Primary Examiner* — Scott J Medway
(74) *Attorney, Agent, or Firm* — Oblon, McClelland, Maier & Neustadt, L.L.P.

(57) ABSTRACT

A tubular body includes an elongated inner layer that demarcates a main lumen; a wire reinforcing layer that is formed by winding a reinforcing wire around the inner layer; a resinous elongated sub-tube that is arranged so as to extend along a longitudinal direction of the main lumen outside the wire reinforcing layer and demarcates a sub-lumen having a smaller diameter than the main lumen; a resinous outer layer that sheaths the wire reinforcing layer and the sub-tube; and a retaining wire. An operating wire is movably inserted through the sub-lumen, and has a tip connected to a distal portion of the tubular body. An operating part is operated to pull the operating wire to bend the distal portion of the tubular body. The retaining wire is sheathed by the outer layer, and winds together the sub-tube and the wire rein-
(Continued)

forcing layer. In a medical instrument (catheter), the retaining wire is in contact with a peripheral surface of the sub-tube on both an external diameter side and an outer surface of the wire reinforcing layer.

18 Claims, 6 Drawing Sheets

(52) U.S. Cl.
CPC .... *A61M 25/0084* (2013.01); *A61M 25/0147* (2013.01); *A61M 25/0045* (2013.01); *A61M 25/0136* (2013.01)

(56) References Cited

U.S. PATENT DOCUMENTS

| | | | | |
|---|---|---|---|---|
| 6,143,013 | A * | 11/2000 | Samson | A61M 25/005 604/264 |
| 6,648,854 | B1 * | 11/2003 | Patterson | A61M 25/005 604/524 |
| 2001/0049491 | A1 * | 12/2001 | Shimada | A61M 25/0012 604/95.04 |
| 2004/0122360 | A1 * | 6/2004 | Waldhauser | A61M 25/0012 604/95.04 |
| 2007/0005008 | A1 * | 1/2007 | Honebrink | A61M 25/0147 604/95.04 |
| 2007/0270679 | A1 * | 11/2007 | Nguyen | A61M 25/0043 600/373 |
| 2010/0036363 | A1 * | 2/2010 | Watanabe | A61M 25/0045 604/524 |
| 2010/0314031 | A1 * | 12/2010 | Heideman | A61M 25/0012 156/149 |
| 2012/0277671 | A1 | 11/2012 | Fuentes | |

FOREIGN PATENT DOCUMENTS

| | | | |
|---|---|---|---|
| JP | 2011 251068 | | 12/2011 |
| JP | 2012 16416 | | 1/2012 |
| JP | 4854458 | | 1/2012 |
| JP | 2012016416 A | * | 1/2012 |
| JP | 2012 100829 | | 5/2012 |
| JP | 2012 213627 | | 11/2012 |

* cited by examiner

MEDICAL INSTRUMENT, CATHETER, AND METHOD FOR PRODUCING MEDICAL INSTRUMENT

TECHNICAL FIELD

The present invention relates to a medical instrument, a catheter, and a method for producing a medical instrument.

Priority is claimed on Japanese Patent Application No. 2013-046335, filed Mar. 8, 2013, the content of which is incorporated herein by reference.

BACKGROUND ART

Various elongated medical instruments, such as catheters or endoscopes, that introduce a medium or a device into a body cavity, are known. In recent years, not only the catheters but also the endoscopes which have a distal end portion and capable of being bent to control the direction of entry into a body cavity are provided.

For example, PTL 1 discloses a catheter in which two wire inner cavities (sub-lumens) having a finer diameter than a central inner cavity (main lumen) demarcated by an inner layer are provided around the main lumen to face each other at 180 degrees. A direction-changing wire (hereinafter referred to as an operating wire) is inserted through each sub-lumen, and the tip of the catheter is bent by operating an operating handle on a base end side to pull the operating wire.

More specifically, in the catheter of PTL 1, two polymer tubes that demarcate wire inner cavities (hereinafter referred to as sub-lumens) are laid along an outer surface of a thin inner layer made of a fluorine-based resin material or the like, and the operating wire is inserted through each polymer tube. In PTL 1, some methods of laying the sub-lumen around the inner layer along the axis of the inner layer are described. A first method is a method of arranging the polymer tube along the axis of the inner layer after the polymer tube is preliminarily extrusion-molded. A second method is a method of extrusion-molding the polymer tube along an outer surface of a core wire in which an inner layer is formed around a mandrel while feeding the core wire. A third method is a method of not molding the polymer tube but of injecting a pressurized fluid into molten resin at the time of the extrusion molding of the inner layer, thereby forming the sub-lumen.

In PTL 1, a cylindrical wire-knitted body (hereinafter referred to as a wire reinforcing layer) is further fastened around the sub-lumen. Multiple strands of a wire are woven to form a mesh around the polymer tube laid around the inner layer in the case of the above third method or along the inner layer in the case of the first or second method to make a wire reinforcing layer, and this wire reinforcing layer is fastened. In addition, molten resin for forming an outer layer is impregnated in the wire reinforcing layer to make a catheter sheath.

[PTL 1] Japanese Unexamined Patent Application, First Publication No. 2006-192269

SUMMARY OF INVENTION

The polymer tube defines a path that guides the operating wire from the tip of the catheter to a base end thereof. Therefore, if the polymer tube meanders around the inner layer or within the inner layer, when the operating wire is pulled, an inner wall surface of the polymer tube and the operating wire come into contact with each other, and friction occurs. Various problems occur if the friction occurs between the operating wire and the inner wall surface of the polymer tube. First, the operating wire is worn out and becomes easy to break. Then, the inner wall surface of the polymer tube is worn out, becomes coarse, and friction further increases. Moreover, since the sliding resistance of the operating wire increases, the pulled operating wire is retained by the static friction with the inner wall surface of the polymer tube, and it becomes difficult to restore the bending of the tip of the catheter.

However, in the method disclosed in PTL 1, it was very difficult to form the sub-lumen to be straight. This is because, in the case of the above first or second method, it is difficult to braid the wire reinforcing layer with the polymer tube being laid on the surface of the inner layer along the axis of the catheter and to fasten the wire reinforcing layer. When the wire reinforcing layer is formed of multiple strands of a wire weaved together and this wire reinforcing layer is fastened, it is inevitable that external force is applied to the sub-lumen in the circumferential direction of the inner layer, and it is difficult to keep the sub-lumen straight and parallel to the axis along the inner layer. Additionally, in the case of the third method, it is not easy to extrusion-mold the inner layer while internally forming the sub-lumen so as to be straight over the entire length of the elongated catheter in the longitudinal direction. This is because temporal fluctuations inevitably occur in the injection pressure of the pressurized fluid, and therefore, it is difficult to maintain the formation position of the uncured molten sub-lumen exactly inside the inner layer.

In addition, although a catheter has been shown and described herein, the same problem occurs throughout medical instruments that perform an operation using the operating wire, without being limited to the catheters.

The invention has been made in view of the above problems, and provides a medical instrument, a catheter, and a method for producing a medical instrument that can form a sub-lumen configured to insert an operating wire easily and precisely along an axis.

According to the invention, there is provided a medical instrument including: an elongated tubular body including an elongated inner layer that demarcates a main lumen, a wire reinforcing layer that is formed by winding a reinforcing wire around the inner layer, a resinous elongated sub-tube that is arranged so as to extend along a longitudinal direction of the main lumen outside the wire reinforcing layer and demarcates a sub-lumen having a smaller diameter than the main lumen, and a resinous outer layer that sheaths the wire reinforcing layer and the sub-tube; an operating wire that is movably inserted through the sub-lumen and has a tip connected to a distal portion of the tubular body; and an operating part that is operated to pull the operating wire to bend the distal portion of the tubular body, in which the tubular body further includes a retaining wire that is sheathed by the outer layer and winds together the sub-tube and the wire reinforcing layer, and in which the retaining wire is in contact with a peripheral surface of the sub-tube on both an external diameter side and an outer surface of the wire reinforcing layer.

According to the above medical instrument, the retaining wires winding together the sub-tube that demarcates the sub-lumen, and the wire reinforcing layer are in contact with the peripheral surface of the sub-tube on both the external diameter side and the outer surface of the wire reinforcing layer. For this reason, the arrangement position of the sub-tube arranged outside the wire reinforcing layer can be precisely maintained along the axis.

In addition, according to the invention, there is provided a method for producing a medical instrument. That is, according to the invention, the method includes: a process of winding a reinforcing wire around an elongated main core wire to form a wire reinforcing layer; a process of arranging an elongated sub-core wire covered with a resinous sub-tube on an outer peripheral surface of the wire reinforcing layer along the main core wire, and winding together the arranged sub-core wire and the arranged wire reinforcing layer with a retaining wire; a process of forming an outer layer so as to sheathe both the sub-core wire and the wire reinforcing layer wound together with the retaining wire, and the retaining wire, and forming a tubular body; a process of elongating the sub-core wire to reduce the diameter of the sub-core wire to peel the sub-core-wire off from the sub-tube, and forming a sub-lumen; and a process of extracting the main core wire from the tubular body to form a main lumen.

According to the invention, a technique of forming the sub-lumen configured to insert the operating wire easily and precisely along the axis in the medical instrument is provided.

DESCRIPTION OF EMBODIMENTS

Figure 1:
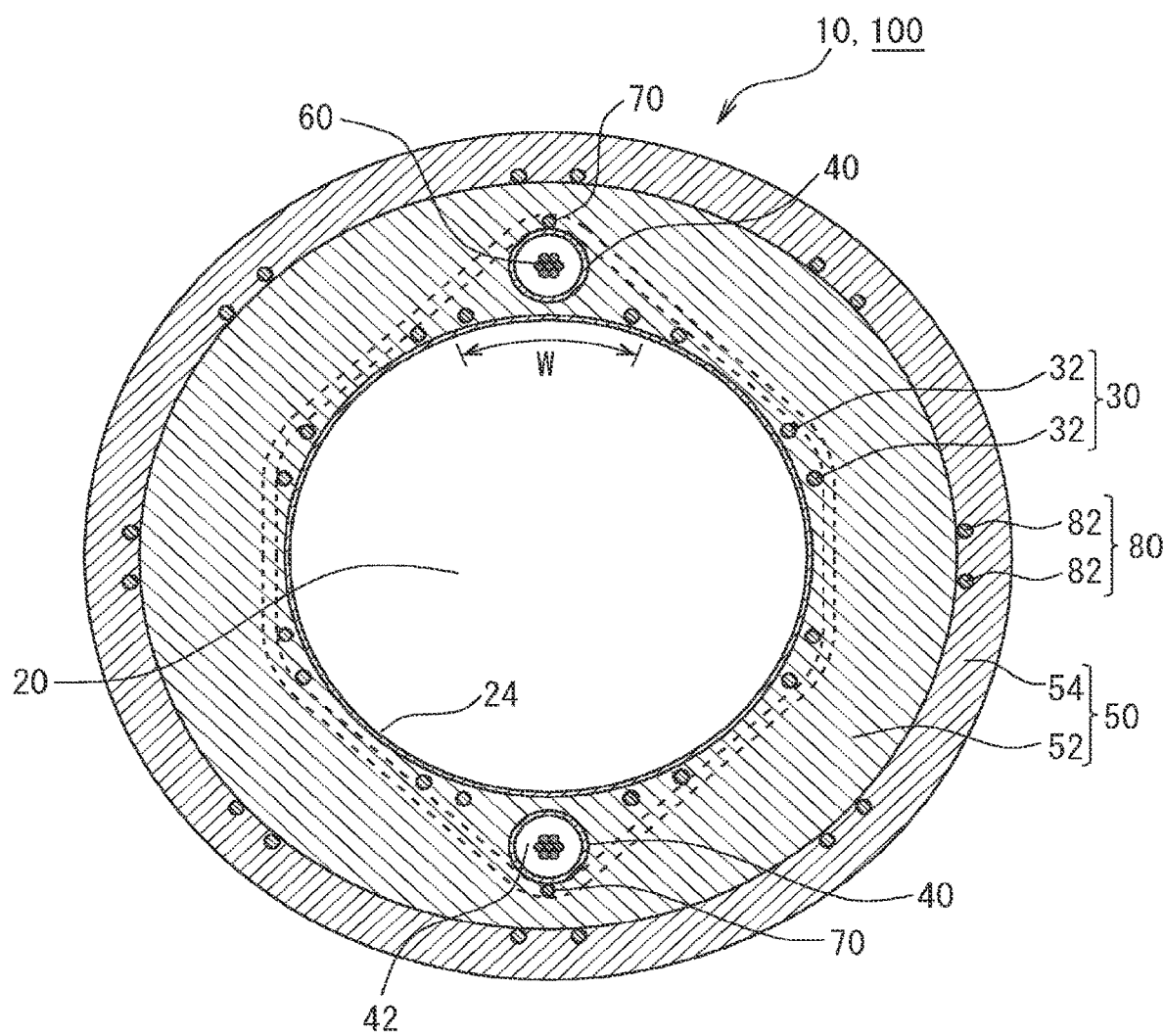
FIG. 1 is a schematic cross-sectional view along line II-II of FIG. 2, in the vicinity of a tip portion of a catheter of an embodiment of the invention.

Hereinafter, an embodiment of the invention will be described with reference to the drawings. In addition, in all the drawings, the same constituent elements will be designated by the same reference numerals, and a detailed description thereof will be appropriately omitted so as not to be duplicated. Additionally, in order to make characterizing portions clearly seen, in all the drawings, scales do not necessarily coincide with actual aspects and scales also vary between the respective drawings.

Figure 2:
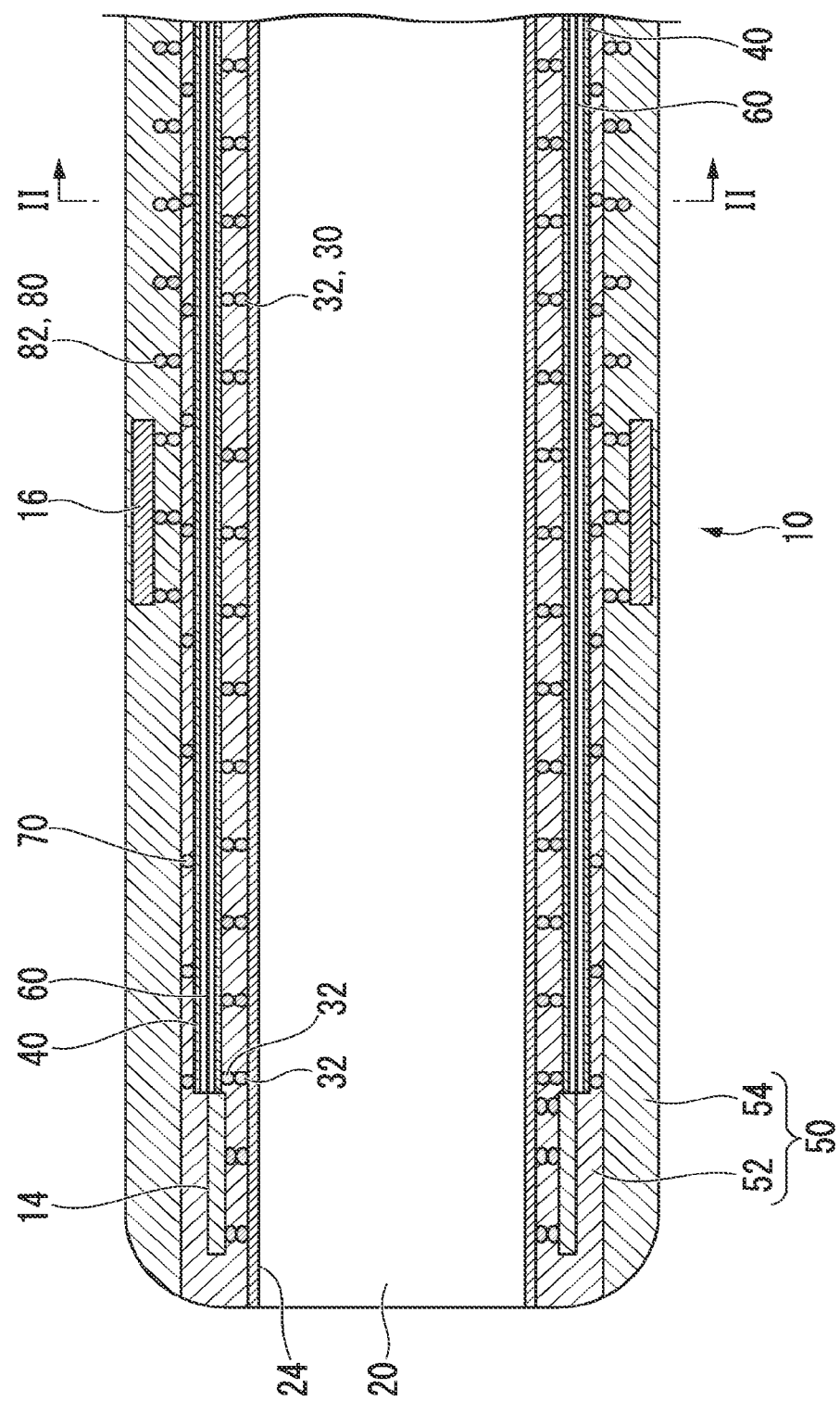
FIG. 2 is a schematic longitudinal sectional view showing the vicinity of the tip portion of the catheter of the embodiment of the invention.

The outline of a medical instrument of the present embodiment will be described with reference to FIGS. 1 to 4. FIG. 1 is a sectional view (cross-sectional view) in which the vicinity of a tip portion of the catheter 100 is cut perpendicularly to a longitudinal direction. FIG. 2 is a sectional view (longitudinal sectional view) in which the vicinity of the tip portion of the catheter 100 is cut along the longitudinal direction. FIG. 1 is a sectional view along line II-II of FIG. 2.

In the present embodiment, a catheter 100 is shown as the medical instrument. The invention can be applied to endoscopes and other medical instruments in which an operating wire 60 can be pulled to bend a distal portion DE, in addition to the catheter 100. In addition, in the invention, a tip (portion) or a distal end (portion) means a terminal (portion) opposite to a side connected to an operating part 90 of a tubular body 10, and the vicinity of the tip portion or the vicinity of the distal portion means a certain region including the tip (distal end). The distal portion DE is a region bent by the operation of the operating wire 60 in the vicinity of the tip portion (vicinity of the distal portion).

The catheter 100 of the present embodiment includes the elongated tubular body 10, the operating wire 60, and the operating part 90. The tubular body 10 includes an elongated inner layer 24 that demarcates a main lumen 20; a wire reinforcing layer 30 that is formed by winding a reinforcing wire 32 around the main lumen 20 (inner layer 24); a resinous elongated sub-tube 40 that is arranged so as to extend along a longitudinal direction of the main lumen 20 outside the wire reinforcing layer 30 and demarcates a sub-lumen 42 having a smaller diameter than the main lumen 20; a resinous outer layer 50 that sheaths the wire reinforcing layer 30 and the sub-tube 40; and a retaining wire 70. The operating wire 60 is movably inserted through the sub-lumen 42, and has a tip connected to the distal portion DE (the vicinity of the tip portion) of the tubular body 10. The operating part 90 is operated to pull the operating wire 60 to bend the distal portion DE of the tubular body 10. The retaining wire 70 which is sheathed by the outer layer 50, and winds together the sub-tube 40 and the wire reinforcing layer 30.

In the catheter 100 of the present embodiment, the retaining wire 70 is in contact with a peripheral surface (outer surface) of the sub-tube 40 on both an external diameter side and an outer surface of the wire reinforcing layer 30.

Hereinafter, the present embodiment will be described in detail. The catheter 100 of the present embodiment is an intravascular catheter that is used after the tubular body 10 is inserted into a blood vessel.

The tubular body 10 is also referred to as a sheath, and is a hollow tubular elongated member through which a main lumen 20 is formed as a through-hole. More specifically, the tubular body 10 is formed with an external diameter and a length such that the tubular body can be made to enter any one of eight sub-sections of the liver.

The tubular body 10 has a stacked structure. An inner layer 24, a first outer layer 52, and a second outer layer 54 are stacked sequentially from an internal diameter side with the main lumen 20 as a center to constitute principal portions of the tubular body 10. An outer surface of the second outer layer 54 is formed with a hydrophilic layer (not shown). The inner layer 24, the first outer layer 52, and the second outer layer 54 are made of a flexible resin material, are annular, respectively, and have substantially uniform thicknesses, respectively. The first outer layer 52 and the second outer layer 54 may be altogether referred to as the outer layer 50.

The inner layer 24 is an innermost layer of the tubular body 10, and the main lumen 20 is demarcated by an inner wall surface of the inner layer. Although the cross-sectional shape of the main lumen 20 is not particularly limited, the cross-sectional shape is circular in the present embodiment. In the case of the main lumen 20 having a circular section, the diameter of the main lumen may be uniform in the longitudinal direction of the tubular body 10, or may be different depending on the positions thereof in the longitudinal direction. For example, a partial or total length region of the tubular body 10 can be made to have a tapered shape in which the diameter (lumen) of the main lumen 20 is continuously increased from the tip toward the base end.

The material of the inner layer 24 may include, for example, a fluorine-based thermoplastic polymer material. The fluorine-based thermoplastic polymer material can include, specifically, polytetrafluoroethylene (PTFE), polyvinylidene fluoride (PVDF), or perfluoroalkoxy fluororesin (PFA). By making the inner layer 24 of such a fluorine-based polymer material, the delivery performance when supplying a medicinal solution or the like through the main lumen 20 becomes excellent. Additionally, when a guide wire is inserted through the main lumen 20, the sliding resistance of the guide wire is reduced.

The outer layer 50 constitutes the main thickness of the tubular body 10. The outer layer 50 of the present embodiment includes the first outer layer 52 that sheathes the retaining wire 70 and has an annular section, and the second outer layer 54 that is provided around the first outer layer 52 to sheathe a second reinforcing layer 80 and has an annular section.

The wire reinforcing layer 30, the sub-tube 40, and the retaining wire 70 are provided inside the first outer layer 52 corresponding to an inside layer of the outer layer 50 sequentially from the internal diameter side. The second reinforcing layer 80 is provided inside a second outer layer 54 corresponding to an outside layer of the outer layer 50. The second reinforcing layer 80 is in contact with an outer surface of the first outer layer 52. The wire reinforcing layer 30 and the second reinforcing layer 80 are arranged coaxially with the tubular body 10. The second reinforcing layer 80 is spaced apart from the wire reinforcing layer 30 and the sub-tube 40 so as to surround the peripheries of the wire reinforcing layer and the sub-tube.

A thermoplastic polymer material can be used as the material of the outer layer 50. The thermoplastic polymer material may be a nylon elastomer, such as polyimide (PI), polyamide imide (PAI), polyethylene terephthalate (PET), polyethylene (PE), polyamide (PA), polyamide elastomer (PAE), or polyether block amide (PEBA), polyurethane (PU), ethylene-vinyl acetate resin (EVA), polyvinyl chloride (PVC), or polypropylene (PP).

An inorganic filler may be mixed for the outer layer 50. As the inorganic filler, a contrast medium, such as barium sulfate or basic bismuth carbonate, is an exemplary example. By mixing the contrast medium for the outer layer 50, the X-ray contrast performance of the tubular body 10 within a body cavity can be improved.

The first outer layer 52 and the second outer layer 54 are made of the same kind of resin material or different kinds of resin materials. Although a boundary surface between the first outer layer 52 and the second outer layer 54 is clearly seen in FIGS. 1 and 2, the invention is not limited to this. When the first outer layer 52 and the second outer layer 54 are made of the same kind of resin material, the boundary surface between both of the layers may be united in complete harmony. That is, the outer layer 50 of the present embodiment may be constituted as a multilayer in which the first outer layer 52 and the second outer layer 54 are distinguishable from each other, or may be constituted of a monolayer in which the first outer layer 52 and the second outer layer 54 may be integrated with each other.

The wire reinforcing layer 30 is a protective layer that is provided closer to the internal diameter side than the operating wire 60 in the tubular body 10 to protect the inner layer 24. As the wire reinforcing layer 30 is present on the internal diameter side of the operating wire 60, a situation is prevented in which the operating wire 60 breaks the first outer layer 52 and the first inner layer 24 and is exposed to the main lumen 20.

The wire reinforcing layer 30 is formed by winding the reinforcing wire 32. As the material of the reinforcing wire 32, a resin material, such as polyimide (PI), polyamide imide (PAI), or polyethylene terephthalate (PET) of which the shear strength is higher than that of the inner layer 24 and the first outer layer 52, can be used, in addition to a metallic material, such as tungsten (W), stainless steel (SUS), nickel-titanium-based alloy, steel, titanium, copper, titanium alloys, or copper alloys. In the present embodiment, the reinforcing wire 32 includes a thin wire of stainless steel.

The wire reinforcing layer 30 is formed by coiling the reinforcing wire 32 or weaving the reinforcing wire together into a mesh. The number of strands of the reinforcing wire 32, a coil pitch and the number of meshes are not particularly limited. Here, the number of meshes of the wire reinforcing layer 30 means the number of intersections (the number of eyes) per unit length (1 inch) as seen in an extending direction of the reinforcing wire 32. Additionally, a parameter expressed by the following Formula (1) is referred to as the mesh size of the wire reinforcing layer 30 as seen in the extending direction of the reinforcing wire 32.

Mesh size in wire extending direction=Unit length(1 inch)/Number of meshes−Wire diameter of wire (1)

As for the second reinforcing layer 80 to be described below, the mesh size of the second reinforcing layer 80 as seen in the extending direction of the second reinforcing wire 82 is also defined by the above Formula (1).

The reinforcing wire 32 is obliquely wound around the inner layer 24. The angle of the extending direction of the reinforcing wire 32 that is formed with respect to the radial direction of the inner layer 24 is referred to as the pitch angle of the reinforcing wire 32. The pitch angle becomes a small angle when the reinforcing wire 32 is wound at a dense pitch. On the contrary, the pitch angle becomes a large angle near 90° when the reinforcing wire 32 is wound at a shallow angle along an axial center of the tubular body 10. Although the pitch angle of the reinforcing wire 32 of the present embodiment is not particularly limited, and the pitch angle can be 30 degrees or more, and preferably be 45 to 75 degrees.

Here, a parameter expressed by the following Formula (2) is referred to as the mesh size W of the wire reinforcing layer 30 in a circumferential direction (see FIG. 1).

Mesh size $W$ in circumferential direction=(Unit length(1 inch)/Number of meshes−Wire diameter of reinforcing wire 32)×$\sqrt{2}$ (2)

The mesh size W of the wire reinforcing layer 30 in the circumferential direction is the length of a diagonal line in a case where the mesh shape of the wire reinforcing layer 30 as seen in the extending direction of the reinforcing wire 32 is regarded as being square.

A braided layer in which the reinforcing wire 32 is braided is shown as the wire reinforcing layer 30 of the present embodiment. The mesh size W of the wire reinforcing layer 30 (braided layer) in the circumferential direction expressed by the above Formula (2), as shown in FIG. 1, is larger than the external diameter of the sub-tube 40. The first outer layer 52 is impregnated between the wire reinforcing layer 30 and the sub-tube 40. That is, no mesh of the wire reinforcing layer 30 is completely covered with the sub-tube 40 irrespective of the positional relationship between the intersection positions (positions of meshes) of the reinforcing wire 32 that intersect in the shape of a mesh and the sub-tube 40. Accordingly, in a producing process to be described below, the first outer layer 52 is impregnated inside meshes from the periphery of the sub-tube 40, and integrally anchors the inner layer 24, the wire reinforcing layer 30, and the sub-tube 40.

The second reinforcing layer 80 is a protective layer that is provided in the external diameter side and protects the second outer layer 54 from the operating wire 60 among the tubular body 10. As the second reinforcing layer 80 is present on the external diameter side of the operating wire 60, a situation is prevented in which the operating wire 60 breaks the second outer layer 54 and the hydrophilic layer (not shown) is exposed to the outside of the tubular body 10. The second reinforcing layer 80 is formed by coiling the second reinforcing wire 82 or weaving together the second reinforcing wire into a mesh. The above material exemplified as the reinforcing wire 32 of the wire reinforcing layer 30 can be used for the second reinforcing wire 82. The second reinforcing wire 82 and the reinforcing wire 32 are made of the same kind of resin material or different kinds of resin materials. In the present embodiment, a braided layer in which a thin wire made of the same kind of material (stainless steel) as the reinforcing wire 32 is braided in the shape of a mesh is an exemplary example of the second reinforcing wire 82.

The wire diameters of the second reinforcing wire 82 and the reinforcing wire 32 may be the same or may be different from each other. In the present embodiment, the second reinforcing wire 82 and the reinforcing wire 32 have the same wire diameter.

Additionally, although the number of strands of the reinforcing wire 32 that constitute the wire reinforcing layer 30, and the number of strands of the second reinforcing wire 82 that constitutes the second reinforcing layer 80 are not particularly limited, these numbers are considered to be the same number in the present embodiment. In FIG. 1, both of the wire reinforcing layer 30 and the second reinforcing layer 80 are shown as braided layers consisting of wires (the reinforcing wire 32, the second reinforcing wire 82) of sixteen strands, respectively.

The sub-tube 40 is a hollow tubular member that demarcates the sub-lumen 42. The sub-tube 40 is buried inside the outer layer 50 (first outer layer 52). The sub-tube 40 can be made of, for example, a thermoplastic polymer material. The thermoplastic polymer material includes a low-friction resin material, such as polytetrafluoroethylene (PTFE), polyetheretherketone (PEEK), or tetrafluoroethylene-hexafluoropropylene copolymer (FEP).

The sub-tube 40 is made of a material having a higher bending rigidity and Young's modulus than the outer layer 50.

An outer surface of the sub-tube 40 is subjected to etching treatment, such as metallic sodium treatment or plasma treatment. This improves the close contact between the sub-tube 40 and the outer layer 50.

As shown in FIG. 1, two sub-tubes 40 are arranged at 180 degrees around the wire reinforcing layer 30 so as to face each other, and operating wires 60 are inserted through the two sub-tubes 40, respectively. The two sub-tubes 40 are parallel to the direction of the axial center of the tubular body 10.

As shown in FIG. 1, the two sub-tubes 40 are arranged on the same circumference so as to surround the main lumen 20. Instead of the present embodiment, three or four sub-tubes 40 may be arranged at equal intervals around the main lumen 20. In this case, operating wires 60 may be arranged in all the sub-tubes 40, or operating wires 60 may be arranged in some sub-tubes 40.

Each operating wire 60 is slidably and loosely fitted into the sub-tube 40. A tip portion of the operating wire 60 is fixed to the distal portion DE of the tubular body 10. Specifically, the operating wire 60 of the present embodiment is fixed to the vicinity of a first marker 14 to be described below. Since a pulling force is applied to a position that is eccentric from the axial center of the tubular body 10 by pulling the operating wire 60 to a base end side, the tubular body 10 is bent. Since the operating wire 60 of the present embodiment is very thin and has high flexibility, no pushing force is substantially applied to the distal portion DE of the tubular body 10 even if the operating wire 60 is pushed to a distal side.

Although the operating wire 60 may be constituted of a single wire rod, the operating wire may be a stranded wire configured by twisting together a plurality of thin wires. Although the number of thin wires that constitutes one stranded wire of the operating wire 60 is not particular limited, the number of thin wires is preferably three or more. A suitable example of the number of thin wires is seven or three.

Figure 3:
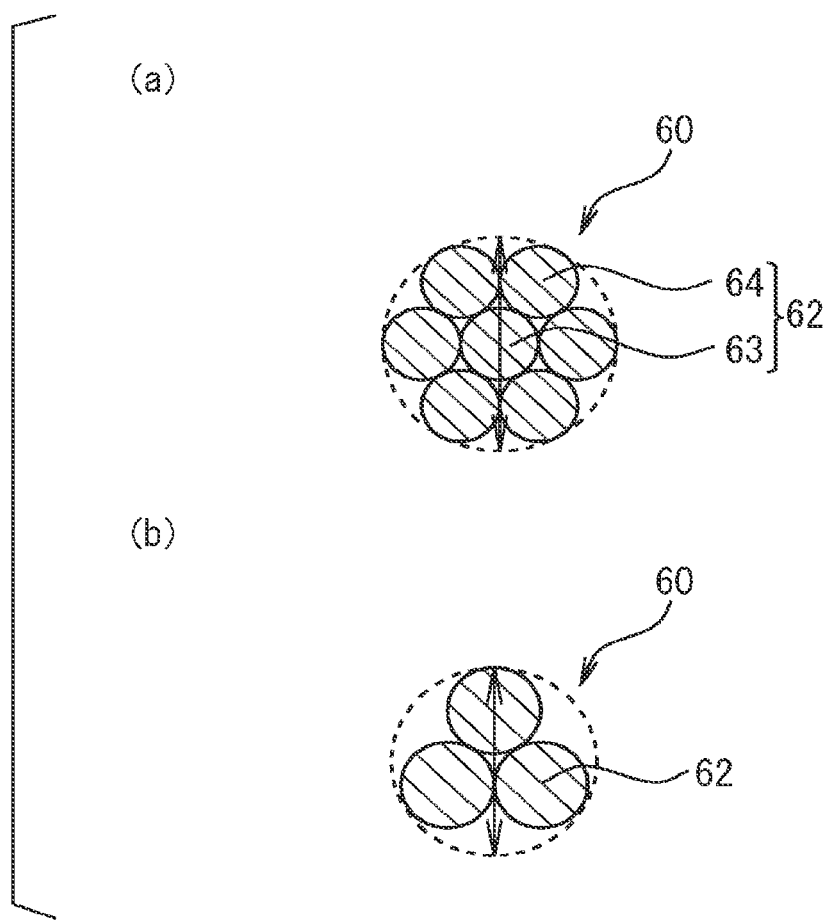
FIG. 3(a) is a cross-sectional view of an operating wire.
FIG. 3(b) is a cross-sectional view of a modification example of the operating wire.

Here, the wire diameter of the operating wire 60 will be described. FIG. 3($a$) is a cross-sectional view of the operating wire 60 of the present embodiment. The operating wire 60 of the present embodiment is a stranded wire in which a plurality of element wires (seven in the present embodiment) 62 are twisted together. More specifically, seven element wires 62 are integrally twisted together by using one element wire (central element wire 63) as a center and spirally winding six element wires (peripheral element wire 64) around the center. Six peripheral element wires 64 are arranged at vertexes of a hexagon centered on the central element wire 63. The wire diameter of the operating wire 60 means the diameter of a circumscribed circle that includes the seven element wires 62 (the central element wire 63 and the peripheral element wires 64) as shown by a double-headed arrow in this drawing.

FIG. 3($b$) is a cross-sectional view of a modification example of the operating wire 60. The operating wire 60 of this modification example is formed by twisting together three element wires 62. The wire diameter of the operating wire 60 in this case also means the diameter of a circumscribed circle that includes the three element wires 62. The wire diameter of the operating wire 60 is shown by a double-headed arrow in this drawing. In addition, it is preferable that the number of element wires 62 is three or seven when a plurality of element wires 62 having the same diameter are twisted together to constitute the operating wire 60. By adopting these numbers of element wires, a state where the element wires 62 are most densely twisted together so as to come into close contact with each other in the circumferential direction and in the radial direction is brought about.

As the operating wire 60 (element wires 62), a metal wire, such as low-carbon steel (piano wires), stainless steel (SUS), steel wires coated with a corrosion-resistant material, titanium, titanium alloys, or tungsten, can be used. In addition, as the operating wire 60 (element wires 62), polyvinylidene fluoride (PVDF), high-density polyethylene (HDPE), poly (para-phenylene benzobisoxazole) (PBO), polyetheretherketone (PEEK), polyphenylene sulfide (PPS), polybutylene terephthalate (PBT), polyimide (PI), polytetrafluoroethylene (PTFE), or polymer fibers, such as boron fibers, can be used.

The retaining wire 70 is a member that winds together the sub-tube 40 and the wire reinforcing layer 30 and is characteristic in the present embodiment. The retaining wire 70 is coiled or braided in the shape of a mesh around the sub-tube 40. Among these, the retaining wire 70 of the present embodiment is a coil, more specifically, a coil (multi-strand coil) in which a plurality of the retaining wires 70 are wound in multiple strands.

The retaining wire 70 is spirally wound so as to surround the outsides of a pair of the sub-tubes 40 arranged to face each other around the main lumen 20. The winding shape of the retaining wire 70 of the present embodiment is a substantially elliptical shape or substantially lozenge shape that has the arrangement direction of the sub-tubes 40 as a major-axis direction. Additionally, the winding shape of the retaining wire may be a polygonal shape. That is, a retaining wire layer formed by winding the retaining wire 70 of the present embodiment around the sub-tubes 40 and the wire reinforcing layer 30 has an elliptical shape, a lozenge shape, or a polygonal shape that has points, which is in contact with the two sub-tubes in the horizontal sectional view (refer to FIG. 1) of the tubular body 10 or the retaining wire layer, as a major axis.

In FIG. 1, the retaining wire 70 (retaining wire layer) in which the winding shape is a polygonal shape (a substantially lozenge shape) shown by the dashed line. The retaining wire 70 (retaining wire layer) is in contact with peripheral surfaces of the sub-tubes 40, specifically, an outside surface corresponding to a side opposite to the axial center of the main lumen 20.

Here, the substantially lozenge shape means that a first diagonal line is longer than a second diagonal line, and the first diagonal line and the second diagonal line are substantially orthogonal to each other. The substantially lozenge shape herein includes flat polygons, such as a kite shape or a flat hexagonal shape, and a flat octagonal shape, in addition to the lozenge shape. Additionally, the substantially elliptical shape and the elliptical shape include an eccentric elliptical shape, such as an egg shape, in addition to the elliptical shape or an oval shape. Additionally, the major axis in the polygonal shape herein means the longest diagonal line among a plurality of diagonal lines of the polygonal shape.

Although an aspect in which the main lumen 20 is circular and is arranged at the center of the tubular body 10 and the two sub-tubes 40 are arranged around the main lumen 20 to face each other at 180 degrees has been shown in the present embodiment, three or more (N) sub-tubes 40 may be equally distributed around the main lumen 20. In this case, the winding shape of the retaining wire 70 may have a corner-rounded N-sided polygonal shape that has the respective sub-tubes 40 as corners.

The retaining wire 70 is in contact with the outer surface of the wire reinforcing layer 30 on both sides or one side in a minor-axis direction (radial direction) orthogonal to the major-axis direction. In the present embodiment, as shown in FIG. 1, the reinforcing wire 32 of sixteen strands is braided such that first eight strands and second eight strands are spirally wound in opposite directions to each other, and the intersection points between the reinforcing wires 32 are formed in eight places in the circumference directions of the inner layer 24. The retaining wire 70 of the present embodiment is in contact with the intersection points between the reinforcing wires 32 so as to ride on the intersection points at positions corresponding to both sides of the winding shape having a substantially lozenge shape in the direction of the minor axis.

The specific winding shape of the retaining wire 70 is determined depending on the physical properties and winding tension of the retaining wire 70. When the ductility of the retaining wire 70 is high and the bending rigidity thereof is low or when the winding tension thereof is large, as shown in FIG. 1, the retaining wire becomes substantially linear between the position (the outside surface of the sub-tube 40) of the major axis and the position (the outer surface of the wire reinforcing layer 30) of the minor axis. In this case, the winding shape of the retaining wire 70 has a substantially lozenge shape. In contrast, when the ductility of the retaining wire 70 is low and the bending rigidity thereof is high or when the winding tension thereof is small, the retaining wire is curved between the position (the outside surface of the sub-tube 40) of the major axis and the position (the outer surface of the wire reinforcing layer 30) of the minor axis. In this case, the winding shape of the retaining wire 70 has a substantially elliptical shape.

An inside surface of the sub-tube 40 is in contact with an outer surface of the wire reinforcing layer 30 (see FIG. 2). That is, the retaining wire 70 is spirally wound around the outside surfaces of the pair of sub-tubes 40 and the wire reinforcing layer 30 in contact therewith. Particularly, the retaining wire 70 of the present embodiment is in contact with the outer surface of the wire reinforcing layer 30 on both sides in the direction of the minor axis. Accordingly, the retaining wire 70 winds together the sub-tube 40 and the wire reinforcing layer 30 such that the sub-tube and the wire reinforcing layer are brought into close contact with each other without being loosened. For this reason, even if the sub-tube 40 undergoes a molding process of the outer layer 50, the sub-tube can maintain a parallel state with high precision with respect to the wire reinforcing layer 30. That is, as the retaining wire 70 forms an elliptical shape, the retaining wire 70 is wound around the wire reinforcing layer 30 and the sub-tube 40 to apply tension thereto so as to embrace the sub-tube 40 at both ends of the major axis. This prevents the positional deviation of the sub-tube 40 in the circumferential direction of the wire reinforcing layer 30.

As seen in the longitudinal direction of the tubular body 10, the retaining wire 70 is wound over substantially the entire length of the sub-tube 40. Accordingly, the relative positions between the wire reinforcing layer 30 and the sub-tube 40 are fixed by the retaining wire 70 in a state where the pair of sub-tubes 40 is kept parallel to the axis direction of the tubular body 10 along the surface of the wire reinforcing layer 30.

As the material of the retaining wire 70, either the above metallic material or the above resin material capable of being used as the reinforcing wire 32 can be used. In the present embodiment, the retaining wire 70 is made of a different kind of material from the reinforcing wire 32. It is preferable that the ductility of the retaining wire 70 is higher than the ductility of the reinforcing wire 32. Specifically, while austenite-based soft stainless steel (W1 or W2) that is a dull material, and copper or copper alloys are used for the retaining wire 70, tungsten and stainless steel spring steel can be used for the reinforcing wire 32.

By using a high-ductility material for the retaining wire 70, when the retaining wire 70 is coiled or braided in the shape of a mesh (coiled in the present embodiment) around the sub-tube 40, the retaining wire 70 plastically elongates and is deformed without being loosely wound to fix the sub-tube 40. Meanwhile, since the wire reinforcing layer 30 is a member that prevents the occurrence of kink of the tubular body 10 as will be described below, it is preferable to use a highly springy material with a high elastic restoring force.

The tubular body 10 includes the second reinforcing layer 80 formed by winding the second reinforcing wire 82 in a circular sectional shape, outside the retaining wire 70. The second reinforcing layer 80 of the present embodiment is a braided layer in which a metallic thin wire is braided in the shape of a mesh. That is, the tubular body 10 of the present embodiment includes a metal layer of three layers referred to as the wire reinforcing layer 30, the retaining wire 70, and the second reinforcing layer 80.

The second reinforcing layer 80 is a member that applies bending elasticity to the tubular body 10 together with the wire reinforcing layer 30. When the tensile load of the operating wire 60 is removed after the distal portion DE of the tubular body 10 is bent by the pulling operation of the operating wire 60, it is preferable that the tubular body 10 is elastically restored. For this reason, in the tubular body 10 of the present embodiment, it is preferable that a springy metallic material is used for the wire reinforcing layer 30 (reinforcing wire 32) and the second reinforcing layer 80 (second reinforcing wire 82). Therefore, the ductility of the retaining wire 70 is higher than the ductility of the reinforcing wire 32 and the second reinforcing wire 82.

The retaining wire 70 is a member for retaining and fixing the sub-tube 40 with respect to the wire reinforcing layer 30, and its effect of reinforcing the tubular body 10 is low compared to the wire reinforcing layer 30 and the second reinforcing layer 80. For this reason, in the present embodiment, as shown in FIG. 2, the winding pitch of the retaining wire 70, that is, the loop interval between the adjacent retaining wires 70, is made larger than any of the pitch intervals of the wire reinforcing layer 30 (reinforcing wire 32) and the second reinforcing layer 80 (second reinforcing wire 82). The pitch interval herein means the interval in the direction of the axial center of the tubular body 10 between the adjacent reinforcing wires 32 or between the second reinforcing wires 82 that are wound in the same direction. However, instead of the present embodiment, the loop interval between the adjacent retaining wires 70 may be smaller than one or both of the pitch intervals of the wire reinforcing layer 30 (reinforcing wire 32) and the second reinforcing layer 80 (second reinforcing wire 82). Accordingly, the sub-tube 40 and the wire reinforcing layer 30 can be suitably retained by the retaining wire 70. Additionally, the loop interval between the adjacent retaining wires 70 may be larger than the pitch interval of the wire reinforcing layer 30 (reinforcing wire 32) and smaller than the pitch interval of the second reinforcing layer 80 (second reinforcing wire 82).

The wire diameter of the retaining wire 70 is smaller than the wire diameter of the operating wire 60. That is, it is sufficient if the retaining wire 70 that ties the sub-tube 40 to the wire reinforcing layer 30 inside the outer layer 50 has a finer diameter than the operating wire 60 in which a pulling force for pulling the distal portion DE of the tubular body 10 is loaded. By making the retaining wire 70 have a finer diameter than the operating wire 60, the thickness of the outer layer 50 in which the retaining wire 70 is embedded can be suppressed, and loose winding of the retaining wire 70 wound around the sub-tube 40 can also be reduced.

A first marker 14 and a second marker 16 located closer to the proximal side than the first marker 14 are provided in the vicinity of a distal portion of the tubular body 10. The first marker 14 and the second marker 16 are ring-shaped members made of a material, such as platinum, through which radiation, such as X rays, is not transmitted. By using the positions of the two markers including the first marker 14 and the second marker 16 as indexes, the position of the tip of the tubular body 10 in a body cavity (blood vessel) can be viewed under the observation of the radiation (X rays). Accordingly, an optimum timing for performing the bending operation of the catheter 100 can be easily determined.

The tip portion of the operating wire 60 is fixed to the portion of the tubular body 10 closer to the distal side than the second marker 16. By pulling the operating wire 60, the portion (distal portion DE) closer to the distal side than the second marker 16 in the vicinity of the distal portion is bent. In the catheter 100 of the present embodiment, the tip portion of the operating wire 60 is fixed to the first marker 14. An aspect in which the operating wire 60 is fixed to the first marker 14 is not particularly limited, and can include solder joint, thermal fusion, adhesion using an adhesive, mechanical latching between the operating wire 60 and the first marker 14, or the like.

The internal diameter of the second marker 16 is larger than the internal diameter of the first marker 14. The first marker 14 is arranged so as to come into contact with or substantially come into contact with the outer surface of the wire reinforcing layer 30. The internal diameter of the first marker 14 is larger than the external diameter of the wire reinforcing layer 30 and smaller than the internal diameter of the second reinforcing layer 80.

The positional relationship in the radial direction between an inner wall surface and an outer peripheral surface of the first marker 14, and the sub-tube 40 is not particularly limited. When the operating wire 60 is fixed to the outer peripheral surface of the first marker 14, as shown in FIG. 2, the external diameter of the first marker 14 can be set such that the outer peripheral surface of the first marker 14 is located inside (on the internal diameter side) the arrangement position of the tip of the sub-tube 40. In addition, when the operating wire 60 is fixed to an end surface of the first marker 14 on the base end side, the end surface may overlap the tip of the sub-tube 40 in the direction of the axial center. In this case, the outer peripheral surface of the first marker 14 may be located closer to the external diameter side rather than the arrangement position of the tip of the sub-tube 40.

The second marker 16 is arranged so as to come into contact with or substantially come into contact with an outer surface of the second reinforcing layer 80. The internal diameter of the second marker 16 is larger than the external diameter of the second reinforcing layer 80.

As shown in FIG. 2, a distal end of the wire reinforcing layer 30 reaches an arrangement region of the first marker 14. The arrangement region of the first marker 14 is a length region where the first marker 14 is formed, as seen in the direction of the axial center of the tubular body 10. The same also applies to the arrangement region of the second marker 16. A distal end of the wire reinforcing layer 30 is located closer to the distal side of the tubular body 10 than a proximal end of the first marker 14. Additionally, the distal end of the wire reinforcing layer 30 is located in the vicinity of a distal end of the first marker 14. In this way, as the wire reinforcing layer 30 reaches the arrangement region of the first marker 14, the discontinuity of the bending rigidity of the tubular body 10 at the proximal end of the first marker 14 can be relaxed to prevent the occurrence of kink.

A distal end of the second reinforcing layer 80 is located closer to the proximal side than the proximal end of the first marker 14 and closer to the distal side than a distal end of the arrangement region of the second marker 16. The distal end of the second reinforcing layer 80 is located in the vicinity of a distal end of the second marker 16. Accordingly, discontinuity is made to occur in the bending rigidity of the tubular body 10 at the distal end of the second marker 16. For this reason, when the pulling operation of the operating wire 60 is performed, the tubular body 10 can be sharply bent slightly closer to the distal side than the second markers 16. In addition, even if the tubular body 10 is sharply bent in this way, kink does not occur in the tubular body 10 because the wire reinforcing layer 30 is continuously formed up to the arrangement region of the first marker 14 as described above. In other words, either the wire reinforcing layer 30 or the second reinforcing layer 80 is continuously formed up to the vicinity of the distal end of the tubular body 10 to prevent kinks, and the other is terminated in the middle of the distal portion DE to cause the discontinuity of the bending rigidity in the tubular body 10 to define the bending position clearly.

Proximal ends of the wire reinforcing layer 30 and the second reinforcing layer 80 are located at a proximal end of the tubular body 10, that is, inside the operating part 90.

A distal end of the inner layer 24 may reach to the distal end of the tubular body 10, or may be terminated closer to the base end side rather than the distal end. The position where the inner layer 24 is terminated may be inside the arrangement region of the first marker 14.

In addition, the invention is not limited to the above embodiment, and alternations, improvements, or the like within the scope that the object of the invention can be achieved will be included in the invention.

In the above embodiment, the wire reinforcing layer 30 is a braided layer, and is shown as a wire reinforcing layer in which the first outer layer 52 is impregnated inside the meshes of the wire reinforcing layer 30 from the periphery of the sub-tube 40, and the inner layer 24, the wire reinforcing layer 30, and the sub-tube 40 are integrally anchored. Instead of this, the first outer layer 52 corresponding to the inside layer of the outer layer 50 does not need to be substantially impregnated between the wire reinforcing layer 30 and the sub-tube 40. That is, the external diameter of the sub-tube 40 may be larger than the mesh size W of the wire reinforcing layer 30 in the circumferential direction, which is expressed by the above Formula (2). Then, the meshes directly under the sub-tube 40 may be meshes which are closed by the sub-tube 40 and in which the first outer layer 52 has cavity portions that are not completely filled.

The hydrophilic layer formed on the outer surface of the second outer layer 54 constitutes an outermost layer of the catheter 100 (tubular body 10). The hydrophilic layer may be formed over the entire length of the tubular body 10, or may be formed only in a partial length region on the tip side including the distal portion DE. The hydrophilic layer is made of, for example, maleic anhydride-based polymers, such as polyvinyl alcohol (PVA) and its copolymers, or a hydrophillic resin material, such as polyvinyl pyrrolidone.

The typical dimensions of the constituent elements of the catheter 100 of the present embodiment will be described.

The diameter of the main lumen 20 can be 400 μm to 600 μm (including an upper limit and a lower limit; the same applies below), the thickness of the inner layer 24 can be 5 μm to 30 μm, and the thickness of the outer layer 50 can be 10 μm to 200 μm. The thickness of the sub-tube 40 can be smaller than that of the inner layer 24, and can be 1 μm to 10 μm. The internal diameter of the wire reinforcing layer 30 can be 410 μm to 660 μm, the external diameter of the wire reinforcing layer 30 can be 450 μm to 740 μm, the internal diameter of the second reinforcing layer 80 can be 560 μm to 920 μm, and the external diameter of the second reinforcing layer 80 can be 600 μm to 940 μm.

The internal diameter of the first marker 14 can be 450 μm to 740 μm, the external diameter of the first marker 14 can be 490 μm to 820 μm, the internal diameter of the second marker 16 can be 600 μm to 940 μm, and the external diameter of the second marker 16 can be 640 μm to 960 μm. The width dimension (the dimension of the tubular body 10 in the longitudinal direction) of the first marker 14 can be 0.3 mm to 2.0 mm, and the width dimension of the second marker 16 can be 0.3 mm to 2.0 mm.

The radius (distance) from the axial center of the catheter 100 to the center of the sub-tube 40 can be 300 μm to 450 μm, the internal diameter (diameter) of the sub-tube 40 can be 40 μm to 100 μm, and the thickness of the operating wire 60 can be 25 μm to 60 μm.

The diameter of the tubular body 10 is 700 μm to 980 μm, that is, the external diameter is less than 1 mm in diameter such that the tubular body can be inserted through a blood vessel, such as a celiac artery.

Figure 4:
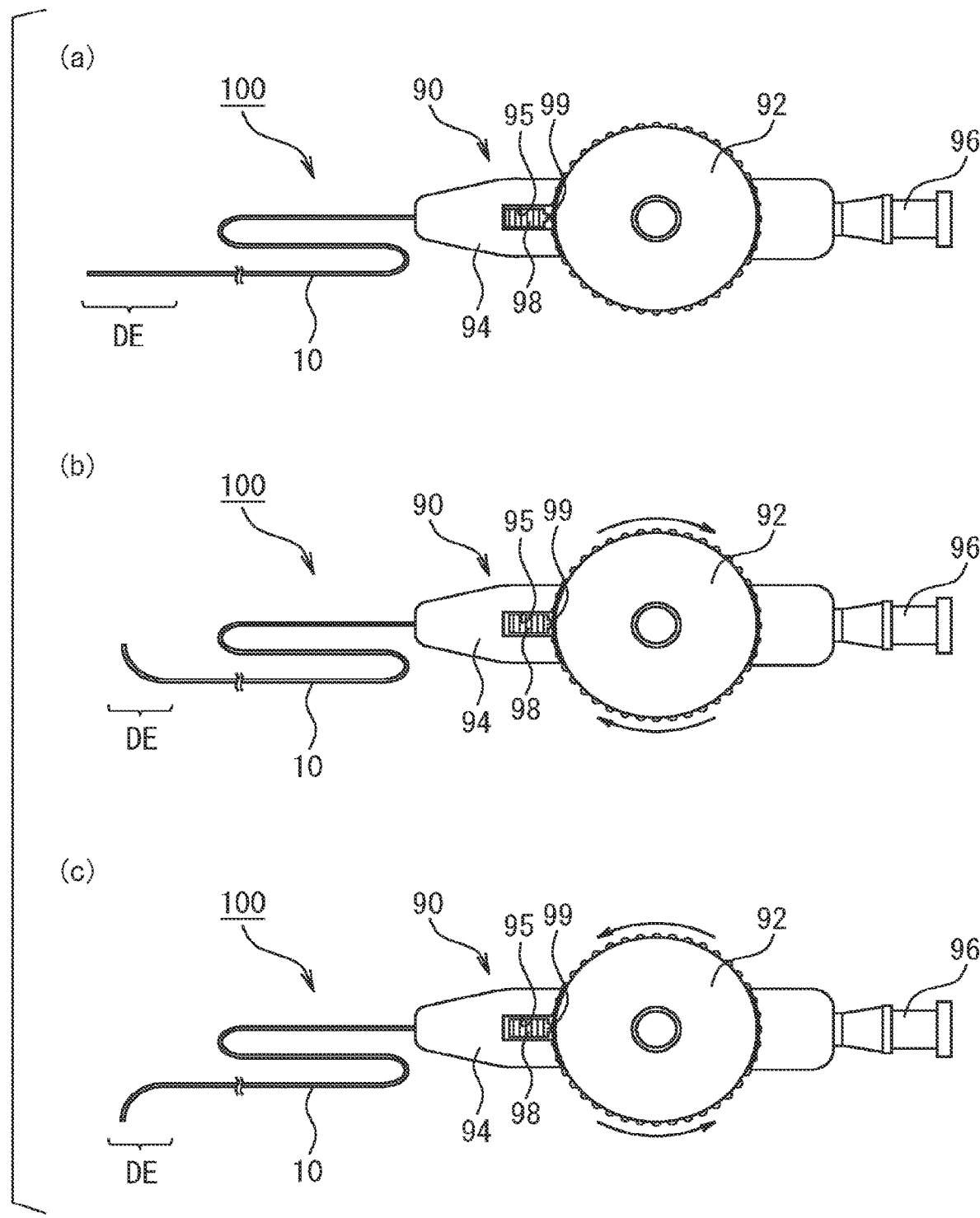
FIG. 4(a) is an overall side view of the catheter of the embodiment of the invention.
FIG. 4(b) is an overall side view of the catheter showing a state where a wheeling portion has been operated in one direction.
FIG. 4(c) is an overall side view of the catheter showing a state where the wheeling portion has been operated in the other direction.

FIG. 4(*a*) is an overall side view of the catheter 100 of the present embodiment. FIG. 4(*b*) is an overall side view of the catheter 100 showing a state where a wheeling portion 92 has been operated in one direction (in a clockwise direction in this drawing). FIG. 4(*c*) is an overall side view of the catheter 100 showing a state where the wheeling portion 92 has been operated in the other direction one direction (in the counterclockwise direction in this drawing).

As shown in FIG. 4(*a*), the catheter 100 has the operating part 90 provided at a base end of the tubular body 10. The operating part 90 constitutes an operating mechanism for performing the bending operation of the distal portion DE of the tubular body 10 together with the operating wire 60 (refer to FIGS. 1 and 2).

The operating part 90 of the present embodiment has a body case 94 that a user grips with his/her hand, and the wheeling portion 92 rotatably provided at the body case 94. The base end of the tubular body 10 is introduced into the body case 94.

The catheter 100 includes a hub 96 that is provided with and communicates with the main lumen 20 of the tubular body 10. A syringe (not shown) is mounted on the hub 96. The hub 96 is provided at a rear end of the body case 94, and the syringe is mounted from the rear (the right of FIG. 4(*a*)) of the hub 96. By injecting a medicinal solution or the like into the hub 96 using the syringe, the medicinal solution or the like can be supplied into a patient's body cavity via the main lumen 20. As the medicinal solution or the like, a contrast medium, a liquid anticancer agent, a physiological salt solution, or n-butyl-2-cianoacrylate (NBCA) used as an instant glue are exemplary examples. In addition, the medicinal solution or the like can include a medical device, such as an embolic coil or beads (embolic spherical substance), without being limited to the liquid.

The operating wire 60 and the sub-tube 40 (refer to FIGS. 1 and 2) branch from the tubular body 10 inside a front end of the body case 94. Base ends of the operating wires 60 pulled out from the two sub-tubes 40, respectively, are directly or indirectly coupled to the wheeling portion 92. By rotationally operating the wheeling portion 92 in any one direction, one of the two operating wires 60 can be pulled to the base end side and can be tensioned, and the other can be loosened. Accordingly, the pulled operating wire 60 bends the distal portion DE of the catheter 100. Specifically, if the wheeling portion 92 is rotated in one direction (clockwise direction) as shown in FIG. 4(b), one operating wire 60 is pulled to the base end side. Then, a pulling force is given to the distal end portion of the catheter 100 via the one operating wire 60. Accordingly, the distal portion DE of the tubular body 10 is bent toward the sub-tube 40 side where the one operating wire 60 is inserted, with the axial center of the tubular body 10 as a reference. Additionally, if the operation of rotating the wheeling portion 92 in the other direction (counterclockwise direction) around a rotating shaft of the wheeling portion is performed as shown in FIG. 4(c), the other operating wire 60 is pulled to the base end side. Then, a pulling force is given to the distal portion DE of the catheter 100 via the other operating wire 60. Accordingly, the distal portion DE of the tubular body 10 is bent toward the sub-tube 40 side where the other operating wire 60 is inserted, with the axial center of the tubular body 10 as a reference.

Here, the tubular body 10 being bent includes an aspect in which the tubular body 10 is bent in a V-shape", and an aspect in which the tubular body is bent like a bow.

In this way, the distal portion DE of the catheter 100 can be selectively bent by selectively pulling the two operating wires 60 through the operation of the operating part 90 with respect to the wheeling portion 92 in a first direction or a second direction included in the same plane.

A peripheral surface of the wheeling portion 92 is formed with a concavo-convex engaging portion. A wave-like vertical knurling tool is shown in the present embodiment. A concave portion 95 is formed at a position that is in contact with the body case 94 at the wheeling portion 92. A concave portion 95 is provided with a slider 98 that slides so as to be capable of advancing and retreating toward the wheeling portion 92. A projection 99 is formed at a tip portion of the slider 98 that faces the wheeling portion 92. The projection 99 is smaller than the opening width of the concavo-convex engaging portion (vertical knurling tool) of the peripheral surface of the wheeling portion 92. If the wheeling portion 92 is made to slide toward the slider 98, the projection 99 is latched to the peripheral surface of the wheeling portion 92, and then rotation of the wheeling portion 92 is regulated. Accordingly, the bending state of the catheter 100 can be maintained by regulating the rotation of the wheeling portion 92 in a state where the distal portion DE of the catheter 100 is bent. FIG. 4(a) shows a state where the projection 99 of the slider 98 and the wheeling portion 92 are in non-engagement and the wheeling portion 92 is rotatable. FIGS. 4(b) and 4(c) show a state where the projection 99 of the slider 98 and the wheeling portion 92 are engaged with each other to regulate the rotation of the wheeling portion 92, and the bending state of the distal portion DE is retained.

By rotating the operating part 90 around the axis of the tubular body 10, the distal portion DE of the tubular body 10 can be rotated with torque at a predetermined angle. Therefore, it is possible to perform the operation of the wheeling portion 92 and the axial rotation of the entire operating part 90 in combination, thereby freely controlling the orientation of the distal portion DE of the catheter 100. Additionally, by adjusting the rotational angle of the wheeling portion 92 to a large or small angle, the pulling length of the operating wire 60 is adjusted to a predetermined value, and the bending angle of the distal portion DE of the catheter 100 can be controlled. For this reason, it is possible to push and advance the catheter 100 into a body cavity, such as a blood vessel that branches at various angles.

Production Method

Figure 5:
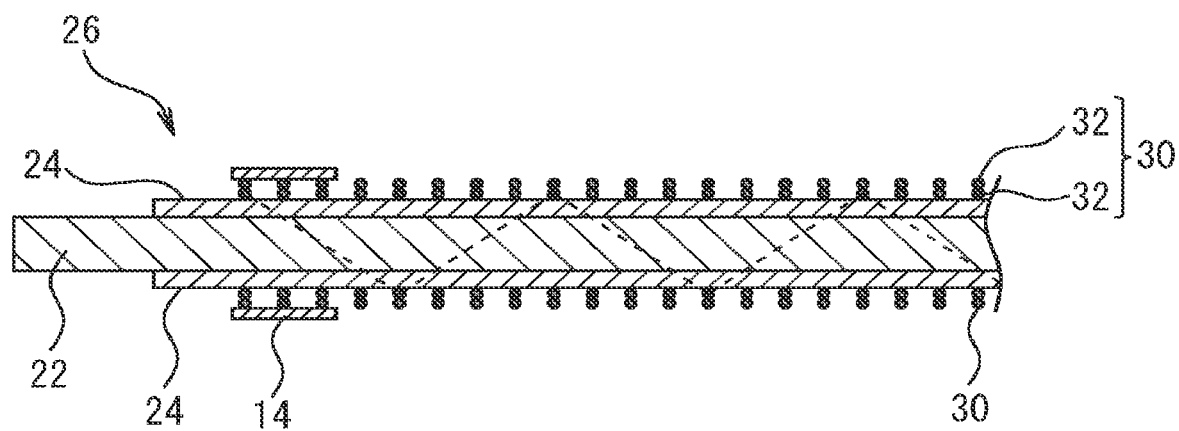
FIG. 5 is a schematic longitudinal sectional view of an inside structure in which an inner layer and a wire reinforcing layer are formed around a main core wire.
Figure 6:
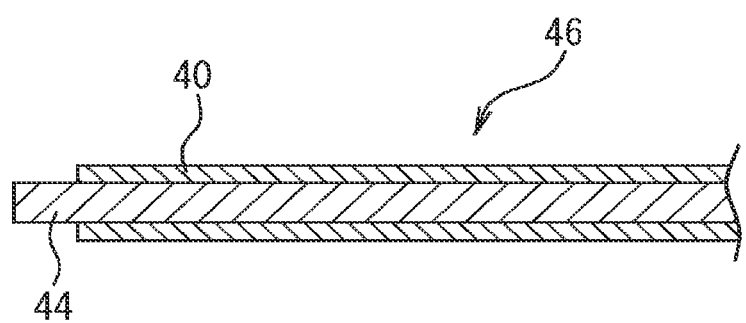
FIG. 6 is a schematic longitudinal sectional view of a cored tube in which a sub-tube is formed around a sub-core wire.
Figure 7:
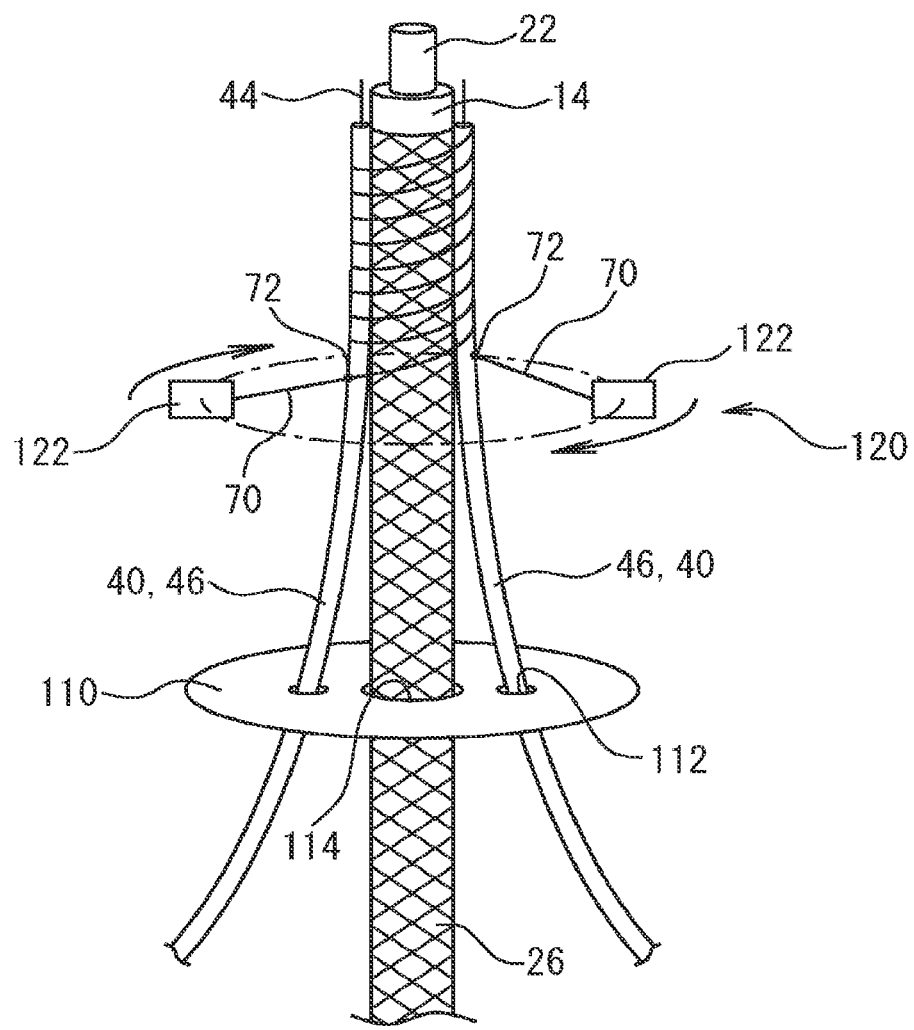
FIG. 7 is a perspective view schematically showing a winding process of a retaining wire.
Figure 8:
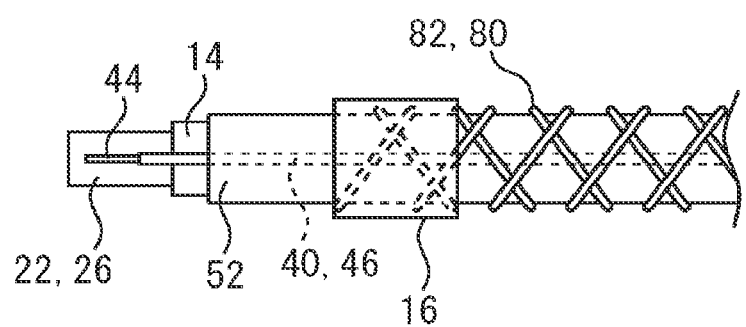
FIG. 8 is a side view showing a state where a second reinforcing wire is wound around the outside of the retaining wire.

Next, a method for producing the catheter 100 of the present embodiment will be described with reference to FIGS. 5 to 8. FIG. 5 is a longitudinal sectional view of an inside structure 26 in which the inner layer 24 and the wire reinforcing layer 30 are formed around the main core wire 22. FIG. 6 is a side view of a cored tube 46 in which the sub-tube 40 is formed around a sub-core wire 44. FIG. 7 is a perspective view schematically showing a winding process of the retaining wire 70. FIG. 8 is a side view showing a state where the second reinforcing wire 82 is wound around the sub-tube 40.

First, the outline of a method (hereinafter may be referred to as the present production method) for producing the catheter 100 that is a medical instrument of the present embodiment will be described.

The present production method includes an inside reinforcing layer making process, a sub-tube retaining process, a body forming process, a sub-core wire extracting process, and a main core wire extracting process. The inside reinforcing layer making process is a process of winding the reinforcing wire 32 around the elongated main core wire 22 to form the wire reinforcing layer 30. The sub-tube retaining process is a process of arranging the elongated sub-core wire 44 covered with the resinous sub-tube 40 on the outer peripheral surface of the wire reinforcing layer 30 along the main core wire 22, and winding together the arranged sub-core wire 44 and the arranged wire reinforcing layer 30 with the retaining wire 70. The body forming process is a process of forming an outer layer so as to sheathe both the sub-core wire 44, the wire reinforcing layer 30 wound together with the retaining wire, and the retaining wire 70, and using the formed outer layer as a tubular body 10. The sub-core wire extracting process is a process of elongating the sub-core wire 44 to reduce the diameter of the sub-core wire to peel the sub-core wire off from the sub-tube 40 to form a sub-lumen 42 (refer to FIG. 1). The main core wire extracting process is a process of extracting the main core wire 22 from the tubular body 10 to form a main lumen 20 (refer to FIG. 1).

Hereinafter, the present production method will be described in detail.

In the inside reinforcing layer making process, first, an inner layer 24 is formed around the main core wire 22. The main core wire 22 is a mandrel (core member), and is a wire rod that demarcates the main lumen 20 and has a circular section. Although the material of the main core wire 22 is not particularly limited, stainless steel can be used. The inner layer 24 can be formed by dipping the main core wire 22 in a coating liquid in which a fluorine-based polymer, such as polytetrafluoroethylene (PTFE), is dispersed in a solvent, and then drying the dripped main core wire. Next, the multiple strands of reinforcing wire 32 are braided to form a mesh on an outer surface of the inner layer 24 to form a wire reinforcing layer 30.

As shown in FIG. 5, the reinforcing wire 32 is excised on the distal side of the first marker 14 after the ring-shaped first marker 14 is crimped and fixed around the tip portion of the reinforcing wire 32. The inside structure 26 is made by the above process.

A cored tube 46 shown in FIG. 6 is made simultaneously with the inside reinforcing layer making process or before or after the inside reinforcing layer making process. In the inside reinforcing layer making process, the sub-tube 40 is formed on the peripheral surface of the sub-core wire 44. The sub-core wire 44 is a wire rod that demarcates the sub-lumen 42 and has a round section. Although the material of the sub-core wire 44 is not particularly limited, the same kind of stainless steel as the main core wire 22 can be used. The sub-core wire 44 has a finer diameter than the main core wire 22. It is preferable that the thickness of the sub-tube 40 is smaller than that of the inner layer 24. When the sub-tube 40 is made of a fluorine-based polymer, such as polytetrafluoroethylene (PTFE), the sub-tube can be formed by dipping the sub-core wire 44 in a coating liquid in which the polymer is dispersed in a solvent, and then drying the dripped sub-core wire.

In addition, the cored tube 46 may be made by pulling down and molding the sub-tube in the shape of a tube such that the internal diameter of the sub-tube 40 becomes larger than the external diameter of the sub-core wire 44, and covering the molded sub-tube around core wire 44.

In the sub-tube retaining process, the sub-core wire 44 is arranged on the outer peripheral surface of the wire reinforcing layer 30 along the main core wire 22, and the retaining wire 70 winds together the sub-core wire and the wire reinforcing layer. In the present production method, a timing at which the sub-core wire 44 is arranged along the main core wire 22, and a timing at which the retaining wire 70 winds together the sub-core wire 44 and the main core wire 22 are substantially simultaneous. As shown in FIG. 7, a plurality of bobbin heads 122 of a winder device 120 are rotated in the same direction around the inside structure 26 while a plurality of the cored tubes 46 is fed along the inside structure 26 through through-holes 112 of an insertion jig 110. The retaining wire 70 is wound around the bobbin head 122. The insertion jig 110 is formed with a main through-hole 114 through which the inside structure 26 is inserted. A pair of through-holes 112 are formed at opposite positions with the main through-hole 114 interposed therebetween.

The main core wire 22 exposed to the tip of the inside structure 26 and the sub-core wires 44 exposed to the tips of the cored tubes 46 are integrally fixed by a jig (not shown). In this state, the first marker 14 is directed to the tip side (upper side of FIG. 7), and the bobbin heads 122 are rotated while pushing out the inside structure 26 and the cored tubes 46 at predetermined feed rates. Accordingly, the retaining wire 70 is wound in a coiled form around the wire reinforcing layer 30 and the sub-tubes 40. The winding pitch of the retaining wire 70 can be increased or decreased by adjusting the feed rate of the inside structure 26 and the rotating speed of the bobbin head 122.

As shown in FIG. 7, when the number of sub-core wires 44 (sub-tubes 40) is two, in the sub-tube retaining process of winding together the sub-core wires 44 and the wire reinforcing layer 30 with the retaining wire 70, the two sub-core wires 44 are arranged on the outer peripheral surface of the wire reinforcing layer 30 to face each other at 180 degrees, and multiple strands of the retaining wire 70 are coiled such that winding points 72 (points where the sub-core wires 44 (sub-tubes 40) of two retaining wires 70 are in contact with each other) thereof are arranged to face each other with the main core wire 22 (inside structure 26) interposed therebetween.

In the present production method, the two sub-core wires 44 are arranged around the wire reinforcing layer 30 to face each other at 180 degrees. When three sub-core wires 44 are arranged, these sub-core wires may be arranged at intervals of 120 degrees. The number of strands of the retaining wire 70 is not particularly limited. The number of strands of the retaining wire can also be two to four regardless of the number of sub-core wires 44. The positions of the plurality of bobbin heads 122 may be selected such that the winding points 72 of the multiple strands of the retaining wire 70 become rotationally symmetrical positions around the wire reinforcing layer 30 as in the present production method. Accordingly, the individual winding tensions of each of the multiple strands of the retaining wire 70 are offset, and an external force that makes the inside structure 26 eccentric is not generated. For this reason, the retaining wire 70 can be wound while maintaining the sub-tubes 40 (cored tubes 46) in parallel along the direction of the axial center of the inside structure 26.

The retaining wire 70 is wound in a substantially elliptical coiled form or a substantially lozenge coiled form that has the outsides of both of the pair of sub-tubes 40 as both ends of the major axis. Since each sub-core wire 44 is inserted into the sub-tube 40, the shape of the sub-tube 40 is circularly maintained against the winding tension of the retaining wire 70.

In addition, although winding around the main core wire 22 in the present production method while feeding the sub-core wires 44 is exemplified, the invention is not limited to the above. After the sub-core wires 44 are temporarily fixed to the main core wire 22 over substantially the entire length in advance by a jig or the like, the retaining wire 70 may wind together the sub-core wires 44 and the main core wire 22.

In the body forming process, the outer layer 50 is formed so as to sheathe the inside structure 26, the cored tubes 46, and the retaining wire 70 (hereinafter, referred to as a structure), thereby forming the tubular body 10. First, the first outer layer 52 is formed around the structure. The first outer layer 52 may be formed by the coating extrusion of coating the surface of the structure with a melted resin material. Otherwise, the first outer layer may be heated and shaped using a heat-shrinkable tube or the like after a resin ring or a resin pipe formed in advance in an annular shape or a tubular shape is mounted around the structure.

Next, the second reinforcing wire 82 is braided around the sub-tubes 40 (cored tubes 46) buried in the first outer layer 52 to the second reinforcing layer 80 (refer to FIG. 8). The second reinforcing wire 82 is excised on the distal side of the second marker 16 after the second marker 16 is crimped and fixed around the tip portion of the second reinforcing layer 80.

Moreover, the second outer layer 54 (refer to FIG. 1) is formed so as cover the second reinforcing layer 80 and the second marker 16. The second outer layer 54 may be formed by the coating extrusion of coating the surface of the second reinforcing layer 80 with a melted resin material, or may be heated and shaped using a heat-shrinkable tube or the like after a resin ring or a resin pipe formed in advance in an annular shape or a tubular shape is mounted around the structure.

In the sub-core wire extracting process, the sub-core wire 44 is elongated to reduce the diameter of the sub-core wire to peel the sub-core wire off from the sub-tube 40. After the diameter-reduced sub-core wire 44 is extracted from the sub-tube 40, the operating wire 60 is inserted into the sub-tube 40. In addition, although the diameter-reduced sub-core wire 44 may be used as the operating wire 60 without being extracted from the sub-tube 40, when the operating wire 60 having a sufficiently smaller diameter than the internal diameter of the sub-tube 40 is used, the sub-core wire 44 may be extracted, and the operating wire 60 different from this sub-core wire may be inserted into the sub-tube 40.

In the main core wire extracting process, the main lumen 20 is formed by extracting the main core wire 22 from the tubular body 10. The sub-core wire extracting process and the main core wire extracting process may be simultaneously performed, or the main core wire extracting process may be performed after the sub-core wire extracting process is first performed. In the latter case, since the elongation and deformation of the tubular body 10 is suppressed by the main core wire 22 being inserted into the main lumen 20, when the sub-core wire 44 is elongated in the sub-core wire extracting process, the sub-tube 40 does not elongate following of the sub-core wire 44. For this reason, the sub-core wire 44 that is easy to break with a finer diameter as compared to the main core wire 22 can be excellently extracted from the sub-tube 40.

In the present production method, the operating part 90 is attached to the base end portion of the tubular body 10 after a hydrophilic layer (not shown) is further formed on the surface of the second outer layer 54. The catheter 100 can be obtained by the above.

In addition, the various constituent elements of the invention do not need to be individually and independently present, and the invention allows a plurality of constituent elements to be formed as one member, one constituent element to be formed by a plurality of members, so that a certain constituent element is a portion of another constituent element, so that a portion of a certain constituent element and a portion of another constituent element overlap each other, or the like.

Additionally, in the present production method, the plurality of processes are described in order. However, the order of the descriptions does not limit the order and timing of the execution of a plurality of processes. For this reason, when the present production method is carried out, the order of the plurality of processes could be changed within a range where there is no difficulty in contents, and some or all of execution timings of the plurality of processes may overlap each other.

The present embodiment and the present production method include the following technical ideas.

(1) A medical instrument including an elongated tubular body includes an elongated inner layer that demarcates a main lumen, a wire reinforcing layer that is formed by winding a reinforcing wire around the inner layer, a resinous elongated sub-tube that is arranged so as to extend along a longitudinal direction of the main lumen outside the wire reinforcing layer and demarcates a sub-lumen having a smaller diameter than the main lumen, and a resinous outer layer that sheaths the wire reinforcing layer and the sub-tube; an operating wire that is movably inserted through the sub-lumen and has a tip connected to a distal portion of the tubular body; and an operating part that is operated to pull the operating wire to bend the distal portion of the tubular body. The tubular body further includes a retaining wire that is sheathed by the outer layer and winds together the sub-tube and the wire reinforcing layer. The retaining wire is in contact with a peripheral surface of the sub-tube on an external diameter side and an outer surface of the wire reinforcing layer, respectively.

(2) The medical instrument according to the above (1) in which the ductility of the retaining wire is higher than the ductility of the reinforcing wire.

(3) The medical instrument according to the above (1) or (2) in which sub-tubes are arranged around the wire reinforcing layer to face each other at 180 degrees, and the operating wires are respectively inserted through the two sub-tubes, and a retaining wire layer in which the retaining wire winds together the sub-tubes and the wire reinforcing layer has an elliptical shape, a lozenge shape, or a polygonal shape having a line obtained by connecting points, which are in contact with the two sub-tubes, as a major axis, in a horizontal sectional view of the tubular body.

(4) The medical instrument according to the above (3) in which the retaining wire layer is in contact with an outer surface of the wire reinforcing layer on both sides or one side in a radial direction orthogonal to the major axis.

(5) The medical instrument according to any one of the above (1) to (4) in which multiple strands of the retaining wire layer are wound together to form a coil wound.

(6) The medical instrument according to the above (5) in which the wire diameter of the retaining wire is smaller than the wire diameter of the operating wire.

(7) The medical instrument according to any one of the above (1) to (6), further including a second reinforcing layer formed by winding a second reinforcing wire outside the retaining wire.

(8) The medical instrument according to the above (7) in which the ductility of the retaining wire is higher than the ductility of any one of the reinforcing wire and the second reinforcing wire.

(9) The medical instrument according to the above (7) or (8) in which the outer layer includes a first outer layer that sheathes the retaining wire and has an annular section, and a second outer layer that is provided around the first outer layer, sheathes the second reinforcing layer, and has an annular section.

(10) The medical instrument according to the above (9) in which the wire reinforcing layer is a braided layer formed by weaving together the reinforcing wire, the mesh size of the braided layer in the circumferential direction is larger than the external diameter of the sub-tube, and the first outer layer is impregnated between the wire reinforcing layer and the sub-tube.

(11) The medical instrument according to the above (9) in which the wire reinforcing layer is a braided layer formed by weaving together the reinforcing wire, and the first outer layer is not substantially impregnated between the wire reinforcing layer and the sub-tube.

(12) Provided is a catheter that is the medical instrument according to any one of the above (1) to (11), further including a hub that is provided to communicate with the main lumen. A syringe is mounted on the hub.

(13) Provided is a method for producing a medical instrument including a process of winding a reinforcing wire around an elongated main core wire to form a wire reinforcing layer; a process of arranging an elongated sub-core wire covered with a resinous sub-tube on an outer peripheral surface of the wire reinforcing layer along the main core wire, and winding together the arranged sub-core wire and the arranged wire reinforcing layer with a retaining wire; a process of forming an outer layer so as to sheathe both the sub-core wire and the wire reinforcing layer wound together with the retaining wire, and the retaining wire, and forming a tubular body; a process of elongating the sub-core wire to reduce the diameter of the sub-core wire to peel the sub-core-wire off from the sub-tube, and forming a sub-lumen; and a process of extracting the main core wire from the tubular body to form a main lumen.

(14) The method for producing a medical instrument according to the above (13) in which, in the process of winding together the sub-core wire and the wire reinforcing layer with the retaining wire, two sub-tubes are arranged around an outer peripheral surface of the wire reinforcing layer to face each other at 180 degrees, and multiple strands of the retaining wire are coiled such that points that are in contact with the sub-core wires of two retaining wires are arranged to face each other with the main core wire interposed therebetween.

REFERENCE SIGNS LIST

10: TUBULAR BODY
14: FIRST MARKER

16: SECOND MARKER
20: MAIN LUMEN
22: MAIN CORE WIRE
24: INNER LAYER
26: INSIDE STRUCTURE
30: WIRE REINFORCING LAYER
32: REINFORCING WIRE
40: SUB-TUBE
42: SUB-LUMEN
44: SUB-CORE WIRE
46: CORED TUBE
50: OUTER LAYER
52: FIRST OUTER LAYER
54: SECOND OUTER LAYER
60: OPERATING WIRE
62: ELEMENT WIRE
63: CENTRAL ELEMENT WIRE
64: PERIPHERAL ELEMENT WIRE
70: RETAINING WIRE
72: WINDING POINT
80: SECOND REINFORCING LAYER
82: SECOND REINFORCING WIRE
90: OPERATING PART
92: WHEELING PORTION
94: BODY CASE
95: CONCAVE PORTION
96: HUB
98: SLIDER
99: PROJECTION
100: CATHETER
110: INSERTION JIG
112: THROUGH-HOLE
114: MAIN THROUGH-HOLE
120 WINDER DEVICE
122: BOBBIN HEAD
DE: DISTAL PORTION
W: MESH SIZE IN CIRCUMFERENTIAL DIRECTION

The invention claimed is:

1. A medical instrument, comprising:
an elongated tubular body;
an operating wire movably inserted through the tubular body and having a tip connected to a distal portion of the tubular body; and
an operating part which is operated to pull the operating wire such that the operating wire bends the distal portion of the tubular body,
wherein the tubular body includes an elongated inner layer demarcating a main lumen, a wire reinforcing layer comprising a reinforcing wire wound around the inner layer, a plurality of resinous elongated sub-tubes extending along a longitudinal direction of the main lumen outside the wire reinforcing layer and demarcating a plurality of sub-lumens respectively, a resinous outer layer sheathing the wire reinforcing layer and the sub-tubes, and a wire retaining layer comprising a retaining wire sheathed in the outer layer and wound around the sub-tubes and the wire reinforcing layer, the operating wire is movably inserted through one of the sub-lumens, the retaining wire is in contact with a peripheral surface of the sub-tubes on an external diameter side and an outer surface of the wire reinforcing layer, the sub-tubes is formed such that each of the sub-lumens has a smaller diameter than a diameter of the main lumen and that the sub-tubes are substantially equally distributed around the main lumen, the retaining wire has ductility which is higher than ductility of the reinforcing wire, and the tubular body has a layered structure comprising the inner layer, the wire reinforcing layer, the sub-tubes in the outer layer and the wire retaining layer in the outer layer in an order of the inner layer, the wire reinforcing layer, the sub-tubes in the outer layer and the wire retaining layer in the outer layer.

2. The medical instrument according to claim 1, wherein the retaining wire comprises metallic material which is different from metallic material of the reinforcing wire.

3. The medical instrument according to claim 1, further comprising:
a second operating wire movably inserted through a second one of the sub-lumens,
wherein the plurality of sub-tubes includes two sub-tubes demarcating the one and second one of the sub-lumens respectively and formed around the wire reinforcing layer such that the two sub-tubes are positioned to face each other across the main lumen, the wire retaining layer has one of an elliptical shape, a lozenge shape, and a polygonal shape having a line obtained by connecting points and is in contact with the sub-tubes, as a major axis, in a horizontal sectional view of the tubular body.

4. The medical instrument according to claim 3, wherein in the horizontal sectional view of the tubular body, the wire retaining layer is in contact with an outer surface of the wire reinforcing layer on both sides or one side of the wire retaining layer in a radial direction orthogonal to the major axis of the wire retaining layer.

5. The medical instrument according to claim 1, wherein the retaining wire comprises a plurality of strands wound together and forming a coil.

6. The medical instrument according to claim 5, wherein the retaining wire has a wire diameter which is smaller than a wire diameter of the operating wire.

7. The medical instrument according to claim 1, further comprising:
a second reinforcing layer comprising a second reinforcing wire wound outside the retaining wire.

8. The medical instrument according to claim 7, wherein the retaining wire has ductility which is higher than ductility of the second reinforcing wire.

9. The medical instrument according to claim 7, wherein the outer layer includes a first sub-outer layer which sheathes the retaining wire and has an annular section, and a second sub-outer layer which is formed around the first sub-outer layer such that the second sub-outer layer sheathes the second reinforcing layer and has an annular section.

10. The medical instrument according to claim 9, wherein the wire reinforcing layer is a braided layer comprising the reinforcing wire woven together, the braided layer has a mesh size in the circumferential direction which is larger than an external diameter of each of the sub-tubes, the first sub-outer layer is impregnated between the wire reinforcing layer and the sub-tubes, and the mesh size in the circumferential direction is defined by formula, mesh size W=(unit length of 1 inch)/number of meshes−wire diameter of reinforcing wire)×√2.

11. The medical instrument according to claim 9, wherein the wire reinforcing layer is a braided layer comprising the reinforcing wire woven together, and the first sub-outer layer is not substantially impregnated between the wire reinforcing layer and the sub-tubes.

12. A catheter, comprising:
the medical instrument of claim 1;
a hub communicating with the main lumen; and
a syringe mounted on the hub.

13. The medical instrument according to claim 3, wherein the retaining wire comprises a plurality of strands wound together and forming a coil.

14. The medical instrument according to claim 13, wherein the retaining wire has a wire diameter which is smaller than a wire diameter of the operating wire.

15. The medical instrument according to claim 3, further comprising:
   a second reinforcing layer comprising a second reinforcing wire wound outside the retaining wire.

16. The medical instrument according to claim 15, wherein the retaining wire has ductility which is higher than ductility of the second reinforcing wire.

17. The medical instrument according to claim 15, wherein the outer layer includes a first sub-outer layer which sheathes the retaining wire and has an annular section, and a second sub-outer layer which is formed around the first sub-outer layer such that the second sub-outer layer sheathes the second reinforcing layer and has an annular section.

18. The medical instrument according to claim 17, wherein the wire reinforcing layer is a braided layer comprising the reinforcing wire woven together, the braided layer has a mesh size in the circumferential direction which is larger than an external diameter of the sub-tubes, the first sub-outer layer is impregnated between the wire reinforcing layer and the sub-tubes, and the mesh size in the circumferential direction is defined by formula, mesh size W=(unit length of 1 inch/number of meshes −wire diameter of the reinforcing wire)×√2.

* * * * *